United States Patent [19]
Kankkunen et al.

[11] Patent Number: 5,611,375
[45] Date of Patent: Mar. 18, 1997

[54] ARRANGEMENT FOR OVERFILL PROTECTION OF A CONTAINER FOR ANAESTHETIC LIQUID

[75] Inventors: Jukka Kankkunen; Erkki Heinonen, both of Helsinki, Finland

[73] Assignee: Instrumentarium Corp., Finland

[21] Appl. No.: 373,979

[22] Filed: Jan. 18, 1995

[30] Foreign Application Priority Data

Jan. 24, 1994 [FI] Finland .................. 940340

[51] Int. Cl.$^6$ ............ A61M 16/18; B67D 5/34
[52] U.S. Cl. .............. 141/18; 141/285; 137/38
[58] Field of Search .................. 141/2, 18, 21, 141/59, 285; 137/38, 44

[56] References Cited

U.S. PATENT DOCUMENTS

| | | | |
|---|---|---|---|
| 3,536,108 | 10/1970 | Schreiber . | |
| 3,972,340 | 8/1976 | Miller et al. | 137/38 |
| 4,108,223 | 8/1978 | Hansel | 141/285 X |
| 4,269,213 | 5/1981 | Sasaki | 137/38 |
| 4,444,182 | 4/1984 | Gregory | 137/38 X |
| 4,715,370 | 12/1987 | Altner et al. | 128/204.13 |
| 4,969,584 | 11/1990 | Joulia | 137/38 X |
| 5,144,991 | 9/1992 | Wallroth et al. | 141/18 X |
| 5,186,201 | 2/1993 | Warren | 137/38 |
| 5,249,714 | 10/1993 | Merhar | 137/38 X |
| 5,337,738 | 8/1994 | Heinonen | 128/203.14 |
| 5,398,737 | 3/1995 | Heinonen et al. | 141/285 |

FOREIGN PATENT DOCUMENTS 242979  10/1987  European Pat. Off. .

Primary Examiner—J. Casimer Jacyna
Attorney, Agent, or Firm—Andrus, Sceales, Starke & Sawall

[57] ABSTRACT

The invention relates to an arrangement for overfill protection of a container for anaesthetic liquid, comprising a liquid conduit for supplying anaesthetic liquid to a container for vaporization, and a gas conduit for withdrawing a volume of gas equivalent to the filling of anaesthetic liquid from the container. To prevent overfilling of the container, the liquid conduit from a feed point for anaesthetic liquid to the container comprises an inclined duct portion having an inlet through which the anaesthetic liquid is passed to the inclined duct portion and an outlet through which the anaesthetic liquid is passed out from the duct portion and further to the container. A body is positioned in the inclined duct portion such that said body can move in the inclined duct portion from a first position to a second position and vice versa, depending on the inclined position of the container, said body being adapted to move in front of the outlet when the container is tilted and to shut the outlet.

12 Claims, 2 Drawing Sheets

ARRANGEMENT FOR OVERFILL PROTECTION OF A CONTAINER FOR ANAESTHETIC LIQUID

FIELD OF THE INVENTION

The present invention relates to an arrangement for overfill protection of a container for anaesthetic liquid, comprising a liquid conduit for supplying anaesthetic liquid to a container for vaporization or withdrawing anaesthetic liquid from the container, and a gas conduit for withdrawing a volume of gas equivalent to the filling of anaesthetic liquid from the container or respectively supplying a volume of gas equivalent to the withdrawal of anaesthetic liquid to the container.

BACKGROUND OF THE INVENTION

In anaesthesia, the gaseous anaesthetic agent inhaled by the patient is formed of oxygen, nitrogen, nitrous oxide and an inhalation anaesthetic. Inhalation anaesthetics are typically in liquid form at administration temperatures, and an anaesthetic vaporizer is needed to gasify them. Anaesthetic vaporizers have a liquid container for vaporizing the liquid. The vaporized anaesthetic is further administered for the patient to inhale by means of a carrier gas flow.

Vaporizer containers are provided with flow conduits and valves by way of which inhalation liquid may be added to the container or, when necessary, drained therefrom. Liquid is added and withdrawn either by means of a filling device specific to the anaesthetic or by directly pouring out into a filling hopper. It is characteristic of the filling device that it can only be fixed to the transport bottle for the given anaesthetic liquid and to the vaporizer. The filling device incorporates a liquid flow conduit and a gas flow conduit. When the container is being filled, liquid flows out from the bottle into the container via the flow conduit, and an equivalent volume of gas flows from the container into the bottle, thus preventing subatmospheric pressure from being produced. When the container is emptied, the procedure is reverse.

It is essential for the operation of the vaporizer that the container is not filled over the maximum limit. If the container is overfilled, this may result, depending on the extent of overfilling, either in an overly high anaesthetic content, which may in the worst case rapidly become lethal, or in stopping of the vaporizing, which may cause the patient to awaken too early.

In prior art constructions, anaesthetic containers are provided with overfill protectors automatically cutting off the flow in the gas flow conduit when the liquid container is full. Thus a subatmospheric pressure is produced in the bottle, the liquid cannot flow into the container, and filling is stopped. The above implements are so constructed that the outlet for the gas flow conduit in the liquid container is positioned at the maximum liquid level. Once the liquid has reached this level, either the gas conduit is filled with liquid, thus cutting off the flow, or a valve shutting automatically at the maximum liquid level is provided in the outlet for the gas flow conduit which is on the liquid container side. Such a valve may be e.g. a float in the liquid, rising with the liquid level until it reaches the outlet and shuts the outlet, thus preventing any gas flow through the gas flow conduit from the container. In present-day anaesthetic vaporizers, the above filling device and overfilling protection mechanism is provided in the wall of the liquid container.

The drawback with the prior art arrangements is that in order for them to operate correctly, the liquid container must be correctly positioned. This means that the vaporizer must typically have an upright position. Hence instructions for filling are provided in operator's instructions for the apparatus. If the vaporizer is filled in an inclined position in such a way that the end of the liquid container facing the filling device is located at a higher level, the liquid level at the end facing the filling device is correspondingly lower, with the result that the overfill protector will not be operative until the liquid container is overfilled.

SUMMARY OF THE INVENTION

It is an object of the present invention to provide an arrangement with which the drawbacks of the prior art solutions can be eliminated. This has been achieved with the arrangement of the invention, which is characterized in that the liquid conduit from a feed point for anaesthetic liquid to the container comprises an inclined duct portion having an inlet through which the anaesthetic liquid is passed to the inclined duct portion and an outlet through which the anaesthetic liquid is passed out from the duct portion and further to the container, and that a body is positioned in the inclined duct portion such that said body can move in the inclined duct portion from a first position to a second position and vice versa, depending on the inclined position of the container, said body being adapted to move in front of the outlet when the container is tilted and to shut the outlet.

It is an advantage of the arrangement of the invention that filling of the container is automatically prevented every time the container is tilted, so that overfilling is impossible. A further advantage is the simplicity of the invention, enabling operational reliability and minimum maintenance for the arrangement. On account of its simplicity, the invention will also be very advantageous in use.

BRIEF DESCRIPTION OF THE DRAWINGS

In the following the invention will be described in further detail by means of a preferred embodiment illustrated in the accompanying drawing, in which.

DESCRIPTION OF THE PREFERRED EMBODIMENTS

Figure 1:
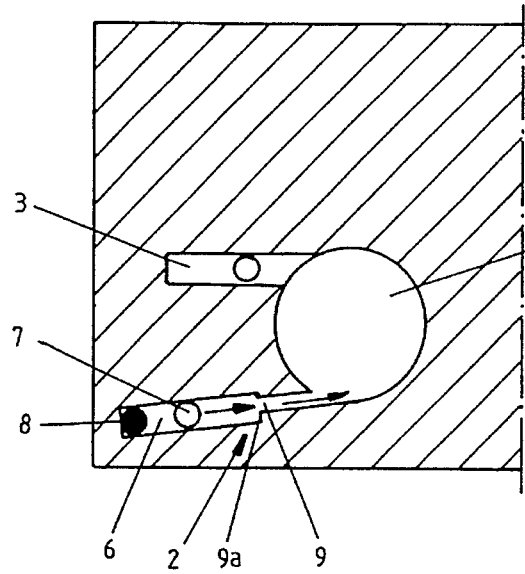
FIG. 1 is a schematic side view of an arrangement of the invention in a normal filling position according to specifications.

FIGS. 1–4 show a preferred embodiment of an arrangement of the invention. Numeral 1 in the figures refers to an anaesthetic container. Reference 2 denotes a liquid conduit for supplying anaesthetic liquid to the container 1 for vaporization or for withdrawing anaesthetic liquid from the container. Reference 3 denotes a gas conduit for withdrawing a volume of gas equivalent to the filling of anaesthetic liquid from the container 1 or respectively for supplying a volume of gas equivalent to the withdrawal of anaesthetic liquid to the container. A feed point for anaesthetic liquid is denoted in FIGS. 2 and 4 generally by reference 5. The feed point 5 may be either a hopper or a filling device specific to the anaesthetic agent.

The supply of anaesthetic liquid to the container for vaporization, the actual vaporization etc. represent fully conventional technology to those skilled in the art, and thus these procedures will not be explained in detail in this context.

The essential feature of the arrangement of the invention is that the liquid conduit 2 from the feed point 5 for anaesthetic to the container 1 comprises an inclined duct portion 6. The inclined duct portion 6 incorporates an inlet 7 through which anaesthetic liquid is passed to said inclined duct portion 6, and an outlet 9 through which the anaesthetic liquid is withdrawn from said duct portion 6 and passed further to the container 1. In this embodiment, the inclined duct portion 6 is adapted to decline away from the container 1. Furthermore, a body 8 is positioned in the inclined duct portion 8 such that said body 8 can move in the inclined duct portion 6 from a first position to a second position and vice versa, depending on the inclined position of the container 1. Body 8 is in this embodiment manufactured of a material of a higher density than that of the anaesthetic liquid, and adapted in the first position to move in front of the outlet 9 and to shut the outlet, e.g. by being pressed against a sealing surface 9a provided at the end of the inclined duct portion 6 facing the container, and to prevent the flow of anaesthetic liquid through the liquid duct 2 into the container 1, and adapted in the second position to be pressed against the end of the inclined duct portion 6 facing away from the container 1 and to permit the flow of anaesthetic liquid through the liquid duct 2 into the container 1. The body 8 may be any suitable body, for example a ball, and may be made of any suitable material, such as plastic or metal, for example acid-proof steel, etc. The angle of inclination of the inclined duct portion 6 relative to horizontal can be determined on the basis of the overfill margin of the container 1. A good principle is that the heavier the body 8, the smaller the allowable angle of inclination. A particularly advantageous angle of inclination is substantially in the range 5°–10°, most preferably 5°–10°, at which, for instance, the inclination of the entire anaesthetic apparatus does not prevent filling of the vaporizer yet.

The inlet 7 for the anaesthetic liquid may be located quite freely in the inclined duct portion. In the embodiment of FIG. 1–4, the inlet 7 is provided in the middle region of the inclined duct portion 6. This is, however, not the only possibility, as the inlet may be located at any point between the extreme positions of the body 8. The idea is that the anaesthetic liquid can flow freely into the container when the body 8 does not shut the outlet 9. The inlet 7 may also be located at an end of the duct portion 6, in which case the weight of the body 8 must be so adapted that the body will not move to the shutting position on account of the flow effect of the anaesthetic liquid.

Figure 2:
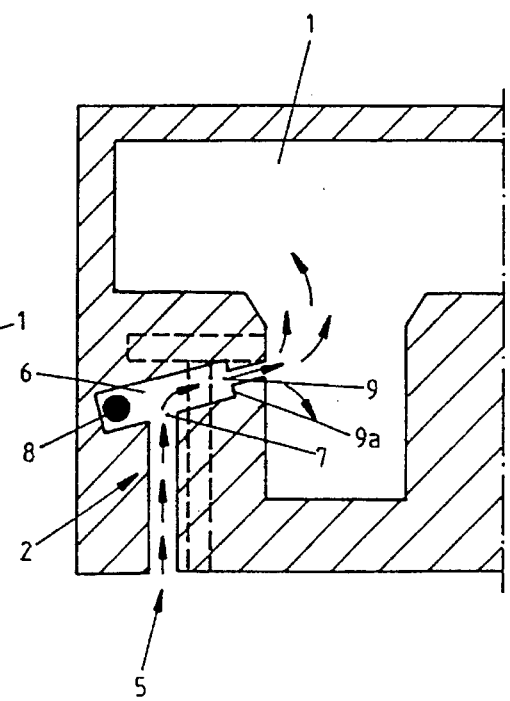
FIG. 2 is a top schematic view of the situation shown in FIG. 1.

As will be seen from the figures, the inclined duct portion 6 is so configured that in the normal filling position it declines toward the feed point 5 for anaesthetic liquid, i.e. toward the filling device. The body 8 within the inclined duct portion 6 is then located at the lower end of the duct portion 6, thus permitting the liquid to flow through the inlet 7 into the duct portion 6 and further into the container 1. This situation is shown in FIGS. 1 and 2. The liquid flow is denoted by arrows in the figures. The essential feature of this embodiment is that in such a situation, the body 8 is located in a region of the duct portion 6 which is outside the liquid flow region, and thus it will not float with the flowing liquid to the end of the duct facing the liquid container, for instance.

Figure 3:
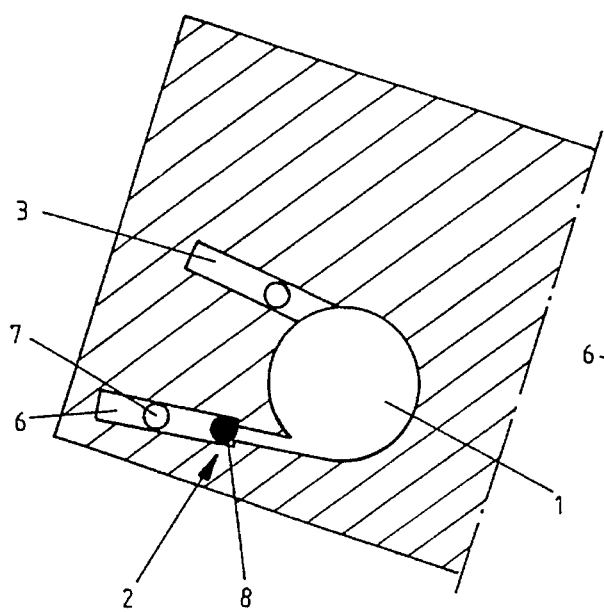
FIG. 3 is a schematic side view of the arrangement of the invention in an inclined filling position.
Figure 4:
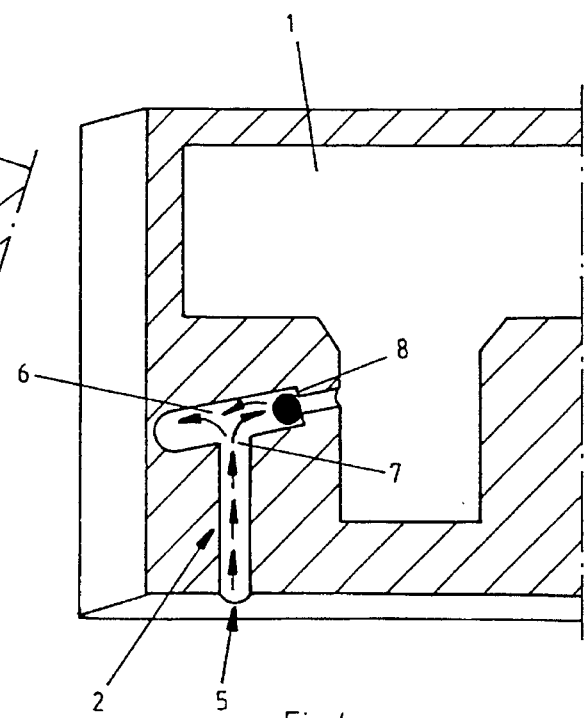
FIG. 4 is a top schematic view of the situation shown in FIG. 3, FIGS. 5 and 6 are schematic views of another arrangement of the invention in a normal filling position according to specifications.

If the liquid container according to this embodiment is tilted so that the feed point 5 for anaesthetic liquid will be located above the liquid container, the inclined duct portion 6 will first turn into a horizontal position and, when tilted further, into a position in which the end facing the liquid container is lower than the end facing away from the liquid container. In that situation, the body 8 in the duct portion 6 will float into a position in which it will be seated against the sealing surface 9a provided at the end facing the liquid container, simultaneously shutting the liquid duct and cutting off the liquid flow into the container. Such a situation is shown in FIGS. 3 and 4. The above will also take place when the container is already inclined when filling is started. Shutting of the liquid duct is thus fully automatic and is dependent only on the position of the container. The liquid duct can be opened by returning the container to an upright position, that is, to the position shown in FIGS. 1 and 2. The inclination that will effect shut-off may be suitably adapted by changing the angle of the inclined duct portion 6 relative to horizontal, as explained previously. If the container is tilted in an opposite direction than above, an overfill protector provided in the gas duct 3 will prevent the filling of the container. The overfill protector positioned in the gas duct represents fully conventional technique to those skilled in the art, and therefore it will not be explained in detail in this context. Suffice it to say that such an overfill protector may be of any known type.

Figure 5:
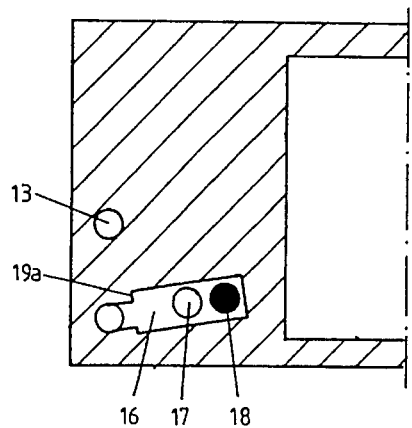
Figure 6:
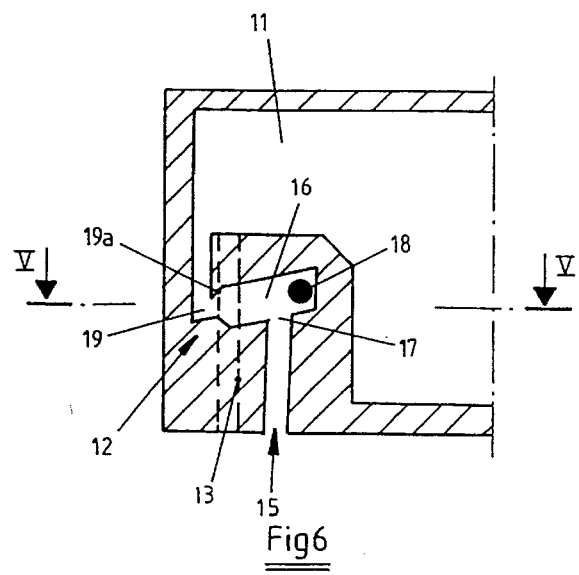
Figure 7:
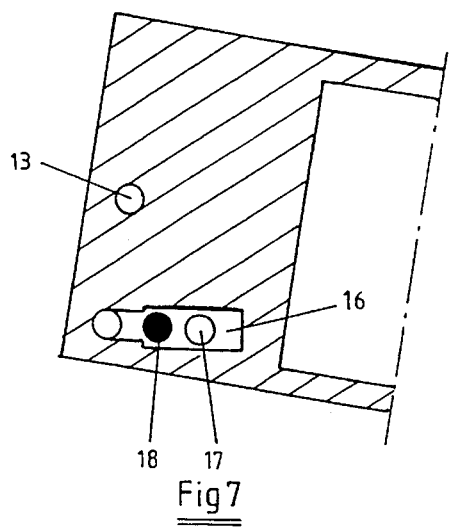
FIG. 7 is a schematic side view of the arrangement of FIGS. 5 and 6 in an inclined position.

FIGS. 5, 6 and 7 show another preferred embodiment of the arrangement of the invention. FIGS. 5, 6 and 7 in principle correspond to FIGS. 1, 2 and 3 illustrating the previous embodiment. FIG. 6 shows an arrangement in accordance with said embodiment in a top schematic view. FIG. 5 is a cross-sectional view along arrows V—V in FIG. 6. In these figures, a container is denoted at 11 and a flow duct for anaesthetic liquid at 12. Reference 13 denotes a gas duct for withdrawal of a volume of gas equivalent to the filling of anaesthetic liquid from the container or respectively for supplying a volume of gas equivalent to the withdrawal of anaesthetic liquid to the container. A feed point for anaesthetic liquid is denoted generally at 15 in the figures. An inclined duct portion provided in the liquid duct 12 is denoted at reference 16. An inlet through which the anaesthetic liquid is supplied to the liquid duct is denoted at 17. A body positioned in the inclined duct portion is denoted at 18. An outlet through which the anaesthetic liquid is conveyed out from the duct portion 16 and further into the container 11 is denoted at 19. Reference 19a denotes a stop face against which the body 18 is pressed upon shut-off of the outlet 19.

The operation of the embodiment of FIGS. 5–7 substantially corresponds to that of the embodiment of FIGS. 1–4. In other words, when the container is tilted the body shuts the outlet through which the anaesthetic liquid flows into the container. The essential feature in the embodiment of FIGS. 5–7 is that the density of the body 18 is lower than the density of the anaesthetic liquid and that the duct portion 16 is adapted to decline towards the container 11.

In this embodiment, the body 18 moves to the upper end of the inclined duct portion when the apparatus is in the horizontal position according to specifications, as shown in FIGS. 5 and 6. In that situation, the anaesthetic liquid can flow freely into the container 11. When the apparatus is tilted so that the end of the inclined duct portion 16 facing the container 11 is located higher than the opposite end of the duct portion, the body 18 will float to the end of the duct portion 16 facing the container 11 and shut the outlet 19, being pressed against the stop face 19a. Such a situation is shown in FIG. 7. If the apparatus is tilted back towards the position shown in FIGS. 5 and 6, the body 18 will move back to the position shown in FIG. 6, for example, once the inclined duct portion is again in a position to decline towards the container 11.

In other respects the embodiment of FIGS. 5–7 corresponds to the embodiment of FIGS. 1–4, and thus reference is made to that embodiment in respect of filling and other corresponding operations.

The body 18 may be manufactured of any suitable material, such as a plastic material. The body 18 may also be made as a shell construction of a plastic or metallic material, filling the interior with a suitable gas.

The embodiments presented above are in no way intended to restrict the invention, but the invention may be modified fully freely within the scope of the claims. Thus it is evident that the arrangement of the invention need not necessarily be precisely as set out in the figures, but other solutions are possible as well. The body provided in the inclined duct portion need not necessarily be a ball, but it is possible to employ e.g. a cylindrical body, etc.

We claim:

1. An arrangement for overfill protection of a container for anaesthetic liquid, comprising a liquid conduit for supplying anaesthetic liquid to a container for vaporization or withdrawing anaesthetic liquid from the container, and a gas conduit for withdrawing a volume of gas equivalent to the filling of anaesthetic liquid from the container or respectively supplying a volume of gas equivalent to the withdrawal of anaesthetic liquid to the container, the liquid conduit from a feed point for anaesthetic liquid to the container comprising an inclined duct portion having an inlet through which the anaesthetic liquid is passed to the inclined duct portion and an outlet through which the anaesthetic liquid is passed out from the duct portion and further to the container, and said arrangement further comprising a body which is positioned in the inclined duct portion such that said body can move in the inclined duct portion from a first position to a second position and vice versa, depending on the inclined position of the container, said body being adapted to move into the first position when the container is tilted more than the angle of inclination of the inclined duct portion and adapted to move into the second position when the container is not tilted more than the angle of inclination of the inclined duct portion, wherein the body prevents the flow of anaesthetic liquid through the liquid conduit into the container when the body is in the first position and the body permits the flow of anaesthetic liquid through the liquid conduit into the container when the body is in the second position;

wherein further the angle of inclination is in the range of 5° to 20°.

2. An arrangement as claimed in claim 1, wherein the body is of a material of a higher density than that of the anaesthetic liquid and the duct portion is adapted to decline away from the container.

3. An arrangement as claimed in claim 2, wherein the angle of inclination of the inclined duct portion relative to horizontal is determined on the basis of the overfill margin of the container.

4. An arrangement as claimed in claim 2, wherein the body positioned in the inclined duct portion is a ball.

5. An arrangement as claimed in claim 1, wherein the body is of a material of a lower density than that of the anaesthetic liquid and the duct portion is adapted to decline towards the container.

6. An arrangement as claimed in claim 5, wherein the angle of inclination of the inclined duct portion relative to horizontal is determined on the basis of the overfill margin of the container.

7. An arrangement as claimed in claim 5, wherein the body positioned in the inclined duct portion is a ball.

8. An arrangement as claimed in claim 1, wherein the angle of inclination of the inclined duct portion relative to horizontal is determined on the basis of the overfill margin of the container.

9. An arrangement as claimed in claim 1, wherein the body positioned in the inclined duct portion is a ball.

10. An arrangement for overfill protection of a container for anaesthetic liquid, comprising a liquid conduit for supplying anaesthetic liquid to a container for vaporization or withdrawing anaesthetic liquid from the container, and a gas conduit for withdrawing a volume of gas equivalent to the filling of anaesthetic liquid from the container or respectively supplying a volume of gas equivalent to the withdrawal of anaesthetic liquid to the container, the liquid conduit from a feed point for anaesthetic liquid to the container comprising an inclined duct portion having an inlet through which the anaesthetic liquid is passed to the inclined duct portion and an outlet through which the anaesthetic liquid is passed out from the duct portion and further to the container, and said arrangement further comprising a body which is positioned in the inclined duct portion such that said body can move in the inclined duct portion from a first position to a second position and vice versa, depending on the inclined position of the container, said body being adapted to move into the first position when the container is tilted more than the angle of inclination of the inclined duct portion and adapted to move into the second position when the container is not tilted more than the angle of inclination of the inclined duct portion, wherein the body prevents the flow of anaesthetic liquid through the liquid conduit into the container when the body is in the first position and the body permits the flow of anaesthetic liquid through the liquid conduit into the container when the body is in the second position;

wherein further the inlet to the inclined duct portion is positioned between the first and second position for the body.

11. An arrangement for overfill protection of a container for anaesthetic liquid comprising:

a container for receiving the anaesthetic liquid;

a liquid conduit for supplying anaesthetic liquid to said container for vaporization or withdrawing anaesthetic liquid from said container;

a gas conduit for withdrawing a volume of gas equivalent to the filling of anaesthetic liquid from the container or, respectively, supplying a volume of gas equivalent to the withdrawal of anaesthetic liquid to the container;

said liquid conduit comprising a duct portion that is inclined when said container is in a predetermined orientation, said duct portion having an inlet through which anaesthetic liquid is received in said duct portion and an outlet through which anaesthetic liquid is discharged from said duct portion, said duct portion extending along a predetermined length between a pair of ends of said duct portion, said inlet opening into said duct portion at a point that is spaced inwardly along said duct portion from one of said ends of said duct portion, said outlet being located proximate the other end of said duct portion, said inlet and outlet being spaced from each other along said duct portion by a predetermined distance to form an anaesthetic liquid flow path along said duct portion between said inlet and outlet that is shorter than said predetermined length of said duct portion; and a flow blocking body positioned in said duct portion for movement along said duct portion responsive to tilting of said container from the predetermined orientation, said body being adapted to move to a first position in said duct portion when the container is tilted less than the inclination of said duct portion, in which first position said body resides in the part of said duct portion between said inlet and said one end of said duct portion and is removed from the flow path in said duct portion between said inlet and outlet, thereby to allow anaesthetic liquid to flow through said duct portion between said inlet and outlet, said body being adapted to move to a second position in said duct portion when the container is tilted more than the inclination of said duct portion, in which second position said body is located between said inlet and said outlet of said duct portion to block said flow path in said duct portion and prevent anaesthetic liquid entering said inlet from leaving said duct portion through said outlet so that overfilling of said container with anaesthetic liquid is avoided.

12. An arrangement for overfill protection of a container for anaesthetic liquid comprising:

a container for receiving the anaesthetic liquid;

a liquid conduit for supplying anaesthetic liquid to said container for vaporization or withdrawing anaesthetic liquid from said container;

a gas conduit for withdrawing a volume of gas equivalent to the filling of anaesthetic liquid from the container or, respectively, supplying a volume of gas equivalent to the withdrawal of anaesthetic liquid to the container;

said liquid conduit having an elongated tubular duct that is inclined when said container is in a predetermined orientation, said duct having an inlet through which anaesthetic liquid is received in said duct and an outlet through which anaesthetic liquid is discharged from said duct, said inlet and outlet being spaced from each other along said duct by a predetermined distance to form an anaesthetic liquid flow path along said duct between said inlet and outlet occupying a first portion of said duct, said duct having a second portion lying outside the fluid flow path of said first portion; and a flow blocking body positioned in said duct for movement along said duct responsive to tilting of said container from the predetermined orientation, said body being adapted to move to a first position in said duct when the container is tilted less than the inclination of said duct, in which first position said body resides in said second portion of said duct and is removed from the fluid flow path in said duct between said inlet and outlet, thereby allowing anaesthetic liquid to flow through said duct between said inlet and outlet, said body being adapted to move to a second position in said duct when the container is tilted more than the inclination of said duct, in which second position said body is located in said first portion of said duct between said inlet and said outlet of said duct to block said flow path in said duct and prevent anaesthetic liquid entering said inlet from leaving said duct through said outlet so that overfilling of said container with anaesthetic liquid is avoided.

* * * * *